United States Patent [19]

Carpenter et al.

[11] 3,985,135

[45] Oct. 12, 1976

[54] DUAL CHAMBER RESERVOIR

[75] Inventors: Walter L. Carpenter, Arlington Heights; Ronald J. Leonard, Harvard, both of Ill.

[73] Assignee: Baxter Laboratories, Inc., Deerfield, Ill.

[22] Filed: Mar. 31, 1975

[21] Appl. No.: 563,861

[52] U.S. Cl. .......... 128/214 D; 229/62.5

[51] Int. Cl.[2] .......... A61M 5/14

[58] Field of Search .......... 128/214; 229/62.5; 150/9

[56] References Cited

UNITED STATES PATENTS

| | | | |
|---|---|---|---|
| 2,663,298 | 12/1953 | Rose | 128/214 D |
| 2,969,063 | 1/1961 | Broman | 128/214.2 |
| 3,746,001 | 7/1973 | Ralston | 128/214 D |

*Primary Examiner*—Lawrence Charles
*Attorney, Agent, or Firm*—Louis Altman; Garrettson Ellis

[57] ABSTRACT

A reservoir for use with blood oxygenation apparatus is described herein. A chamber separator within said reservoir defines, in the interior thereof, a primary chamber and a secondary chamber, with a flow channel, connecting the primary and secondary chambers. A plurality of intake and outlet ports communicate with the primary chamber. The reservoir may be connected to blood oxygenation apparatus via the intake and outlet ports, while the flow channel may be clamped to prevent fluid flow between the primary and the secondary chambers, when it is desired to reduce the blood volume in the reservoir.

4 Claims, 3 Drawing Figures

DUAL CHAMBER RESERVOIR

BACKGROUND OF THE INVENTION

Reservoirs are used in blood oxygenation apparatus for storing variable amounts of blood during the course of the oxygenation procedure, to facilitate changes in flow rate to the oxygenator and the like.

In the past, the priming volume of prior art reservoirs has been customarily large, since a substantial reservoir volume capacity is frequently needed during oxygenation procedures. However, this is undesirable overall, since a large priming volume in the total oxygenation apparatus requires the use of a large amount of donated blood, with the consequent hazard of disease which may be transmitted through the blood, and of course the increased expense and difficulty in obtaining the blood.

Furthermore, gas bubbles in the blood line introduced through the cardiotomy suction apparatus, if used, and from other sources, are generally vented from a vent at the top of a conventional blood reservoir. Often, during the venting, blood will spatter out of the vent onto the exterior of the oxygenation apparatus, which is, of course, undesirable.

Furthermore, in one type of pediatric surgery, the body temperature of the infant is reduced, followed by an almost complete exsanguination of the blood of the infant into the blood oxygenation system. In this circumstance, there is need for the holding capacity of the reservoir, which is desirably small at the beginning of the operation, to be significantly increased to hold the large amount of blood which is removed from the infant.

Furthermore, it is also important that the blood be retained in sterile, blood-compatible condition, and not to be removed from the system where contamination is possible, but it should be stored within the system until return to the infant a short time later after the radical exsanguination procedure is completed.

In accordance with this invention, a reservoir is provided which exhibits an initial low priming volume, yet which can be easily modified, without opening of the reservoir to the exterior, to provide additional blood holding capacity for the various times during which that is desired. Also, the reservoir of this invention contains an internal chamber separator, which shields the vent of the reservoir from the flow currents of blood passing into and out of the reservoir. This avoids spattering of blood through the vent.

Broman U.S. Pat. No. 2,969,063 discloses a flat chamber in a parenteral solution administration set having narrow portions, which may be closed off with a hemostat to meter selected amounts of parenteral solution to the patient. However, such structure has never been used in conjunction with high-flow, bubble trapping blood reservoirs having multiple entry and exit ports.

SUMMARY OF THE INVENTION

In accordance with this invention, a reservoir is provided having particular utility for use in conjunction with blood oxygenation apparatus. The reservoir is divided in its interior by a chamber separator into a primary chamber and a secondary chamber. A plurality of intake and outlet ports communicate with the primary chamber, and are adapted for fluid communication with the remaining parts of the blood oxygenation apparatus as desired. A flow channel provides communication between the primary and secondary chamber, and is of such a size that it may be clamped shut from the exterior, when it is desired to shut off communication between the chambers.

Typically, the reservoir comprises a pair of heat-sealed plastic sheets, peripherally sealed to define an interior space which, in turn, is divided by a pair of angularly related heat seal lines to define the chamber separator. The two heat seals may form an apex, which is spaced from one edge of the space-defining peripheral seal. The flow channel is then defined between the apex and such peripheral seal.

In its operation, the reservoir may be connected to the blood oxygenation apparatus via the intake and outlet ports. When desired, the flow channel is clamped with a hemostat or the like, to prevent fluid communication between the primary and secondary chambers. When the primary chamber is filled with blood and gas for venting, and more reservoir capacity is desired, the flow channel may be unclamped, to allow fluid flow between the primary and secondary chambers.

In the drawings, FIG. 1 is a plan view of the reservoir of this invention.

Figure 1:
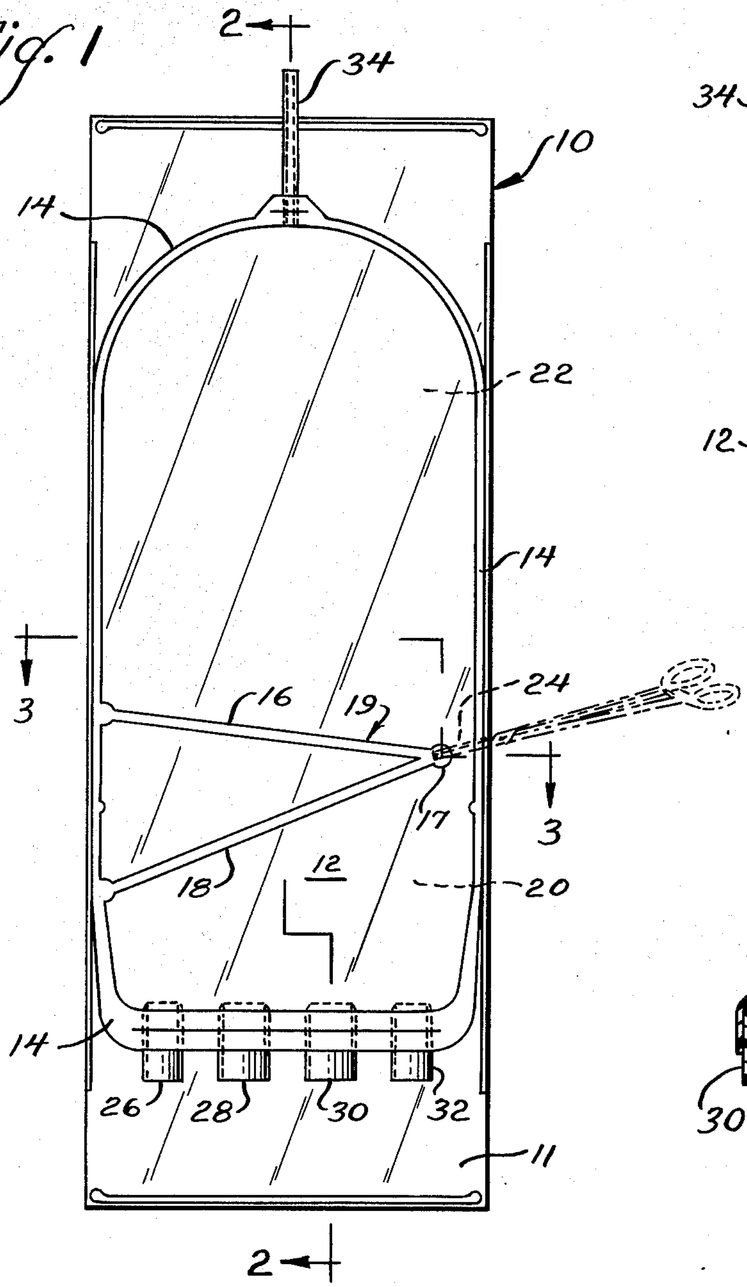
Figure 2:
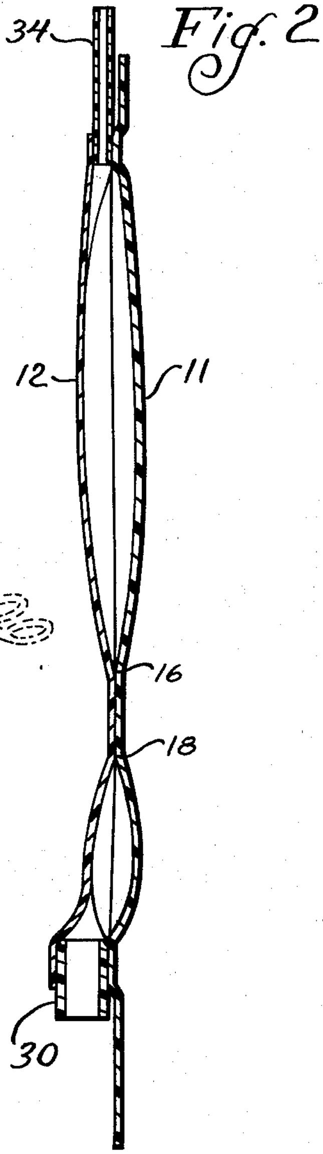
FIG. 2 is a sectional view taken along line 2—2 of the reservoir of this invention.
Figure 3:
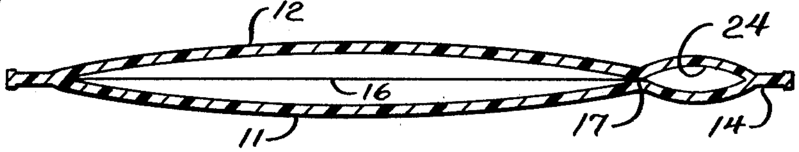
FIG. 3 is a sectional view taken along line 3—3 of the reservoir of this invention.

Referring now to the drawings, reservoir 10 comprises a pair of heat-sealed plastic sheets 11, 12, peripherally sealed about heat seal line 14 to define an interior space.

A pair of seal lines 16, 18 are angularly related to each other, joining together at apex 17, to define chamber separator means 19, which, in turn, defines a primary chamber 20 and a secondary chamber 22. Chamber separator 19 is spaced from seal line 14 in one lateral area to define flow channel 24, for communication between chambers 20 and 22.

A plurality of ports 26, 28, 30 and 32 are defined along a portion of the chamber-defining seal line 14, to provide access between primary chamber 20 and the exterior. Ports 26, 28, 30, 32 pass through seal line 14, and are in sealed relation thereto, so that the only access is through the ports.

Vent tube 34 provides communication between secondary chamber 22 and the exterior, passing in sealed manner through seal line 14.

When it is desired to seal chamber 20 so as to reduce the blood volume of th reservoir, a hemostat or another clamp may be placed across channel 24 to seal it. After priming, and during the course of the operation, if for any reason a larger blood volume is required in the reservoir, or it is desired to vent gases, the hemostat may be removed from its sealing position across channel 24, to provide access between chambers 20 and 22 for storage of additional blood, or for venting. The hemostat of course may be reapplied at any time across channel 24.

Seal line 18, as part of chamber separator 19, is preferably positioned at an angle to the vertical in position of use, as shown in FIG. 1, to provide means for guiding gas bubbles toward channel 24 as they travel upwardly, to facilitate the venting from chamber 20.

Seal line 16 is positioned to point downwardly in position of use toward channel 24, to facilitate the drainage of liquids from chamber 22 when such is desired.

More than one of the reservoirs of this invention may be utilized in an oxygenation process if desired, for example, in the total by-pass membrane oxygenator system recommended by the Artificial Organs division of Travenol Laboratories, Inc. for use in conjunction with porous membrane oxygenators which are currently on sale. One of the reservoirs functions as a venous reservoir while another functions as an arterial reservoir.

For the reservoir of this invention which is to be used as a venous reservoir, port 28 can communicate with the cardiotomy reservoir in the system, which receives blood from the surgical incision site through a cardiotomy suction device. Port 26 may receive blood from the patient's venous supply. Port 32 can communicate with a conduit which passes blood from the venous reservoir to a venous roller pump, and from there to a heat exchanger, then to the oxygenator, and thereafter through the arterial reservoir. Port 30 may communicate directly with the arterial reservoir.

In the reservoir of this invention which is used as an arterial reservoir, port 28 can communicate with port 30 of the venous reservoir. Port 26 may receive blood from the oxygenator, while port 32 can communicate with tubing that passes through the arterial roller pump, from there conveying blood to the arterial system of the patient. The last port 30 may provide blood to a coronary perfusion apparatus, if desired.

Once reservoir 10 is thus connected to the blood oxygenator apparatus in the above-disclosed fashion, reservoir 10 may be operated with flow channel 24 in either an open or closed position. In the initial stages of use, flow channel 24 is customarily closed by clamping the hemostat over flow channel 24. It may be appreciated that a chief advantage of reservoir 10 is the fact that chamber separator 19 defines flow channel 24 in a position immediately adjacent heat seal 14, thereby allowing a small hemostat or clamp to control flow channel 24.

In order to start up the blood oxygenation apparatus, it is necessary to prime blood reservoir 10. Priming of blood reservoir 10 can be accomplished with a minimum volume of blood by clamping flow channel 24 and only filling primary chamber 20. Although the total volume of blood reservoir 10 is large, priming with a small volume of blood in primary chamber 20 may be easily and conveniently accomplished.

During the course of surgery various gases may become entrapped in the blood contained in the blood oxygenator, which must be removed before the blood is recirculated into the patient. Typically, gases are introduced into the blood through the suction line which aspirates the blood from the operative site. Prior blood reservoirs have been provided with a vent to bleed off the excess gases which accumulate as the gases bubble out of the pooled blood in the reservor. The prior reservoirs however often became contaminated, since the bubbling often took place near the vent, carrying blood into the vent, where it may become contaminated, and then fall back into the pooled blood. Blood reservoir 10 prevents this, as flow channel 24 may be opened to allow the gases to escape to secondary chamber 22 and then to vent 50.

It will be noted that ports 26 and 32 are positioned in such a way that the flow of blood through the primary chamber will tend to sweep any gas bubbles towards channel 24 where they may be vented.

In addition, spattering is reduced by the slight upward angle of heat seal line 18 which promotes a smooth and continuous flow of bubbles to flow channel 24.

As stated above, in some types of coronary surgery performed on infants, it is desirable to place the infant in hypothermia and then exsanguinate him. The exsanguination procedure is difficult to perform with blood oxygenators employing conventional reservoirs. Blood reservoir 10 is especially suited to infant exsanguination procedures, since flow channel 24 can be unclamped to receive the exsanguinated blood, and then reclamped during surgery to hold the exsanguinated blood in the reservoir. When the surgical procedure is completed, flow channel 24 is unclamped to allow the exsanguinated blood to flow through flow channel 24 into primary chamber 20 and from there back to the infant patient. The slight downward slope of seal line 16 insures that all exsanguinated blood is returned to the patient.

Furthermore, the use of blood reservoir 10 having a primary chamber 20 with a secondary chamber 22 allows adequate gas removal, while reducing the gas-blood interface area, when the blood level is in substantial contact with seal line 18.

During other types of surgery it may be desirable to begin surgery with a blood reserve which may be selectively added to the blood oxygenator circulation as the need arises. In this case, secondary chamber 22 may be filled with blood before surgery begins, and the extra blood supplied to the blood oxygenation apparatus by merely unclamping flow channel 24.

The above has been offered for illustrative purposes only and is not to be understood as limiting the scope of the invention of this application, which is as defined in the claims below.

That which is claimed is:

1. In a reservoir for receiving and storing blood and the like for a variety of surgical procedues, having intake and outlet ports, and of at least a capacity capable of receiving a major portion of the exsanguinated blood supply of an infant undergoing a hypothermic surgical procedure, said reservoir being made of a pair of plastic sheets sealed together with a peripheral seal, the improvement comprising: chamber separator means dividing the interior of said reservoir into a primary chamber and a secondary chamber, and defining a flow channel providing communication between said primary and secondary chambers, said chamber separator means defining first and second, angularly-related seal lines between said plastic sheets, said lines being spaced transversely to the axis of said reservoir, said lines joining to form an apex which is spaced from the edges of said peripheral seal, to define said flow channel between said apex and one edge of the peripheral seal, said plastic sheets extending between said angularly-related seal lines, and said intake and outlet ports communicating with the primary chamber.

2. The reservoir of claim 1 in which said first, angularly related heat seal line defines an upper edge, in position of use, of the primary chamber, said first heat seal line being slanted upwardly toward said apex to provide guide means for rising gas bubbles in said primary chamber.

3. The reservoir of claim 2 in which said second, angularly related heat seal line defines a lower edge, in position of use, of the secondary chamber, said second heat seal line being slanted downwardly toward said apex to facilitate the complete draining of said secondary chamber.

4. The reservoir of claim 3 which said secondary chamber communicates with a vent tube leading to the exterior through said periphery.

* * * * *